United States Patent [19]
Fenical et al.

[11] Patent Number: 6,069,146
[45] Date of Patent: May 30, 2000

[54] HALIMIDE, A CYTOTOXIC MARINE NATURAL PRODUCT, AND DERIVATIVES THEREOF

[75] Inventors: William Fenical, Del Mar; Paul R. Jensen; Xing C. Cheng, both of San Diego, all of Calif.

[73] Assignee: The Regents of the University of California, Oakland, Calif.

[21] Appl. No.: 09/191,475

[22] Filed: Nov. 12, 1998

Related U.S. Application Data

[63] Continuation-in-part of application No. 09/047,781, Mar. 25, 1998, abandoned.

[51] Int. Cl.⁷ ........................ A61K 31/496; C07D 403/06
[52] U.S. Cl. ............................................. 514/252; 544/370
[58] Field of Search ............................. 544/370; 514/252

[56] References Cited

U.S. PATENT DOCUMENTS 5,891,877  4/1999  Brocchini et al. .................... 514/235.8

FOREIGN PATENT DOCUMENTS 10-130266  5/1998  Japan ........................... C07D 403/06

OTHER PUBLICATIONS

Fukumoto et al., *Chemical Abstracts*, vol. 129, No. 53444 (Abstract for JP 10130266, May 19, 1998), 1999.
Kanoh et al., *Bioorganic & Medicinal Chemistry Letters* vol. 7, No. 22 pp. 2847–2852, 1997.

*Primary Examiner*—Emily Bernhardt
*Attorney, Agent, or Firm*—Campbell & Flores LLP

[57] ABSTRACT

The present invention provides a substantially purified compound having the structure:

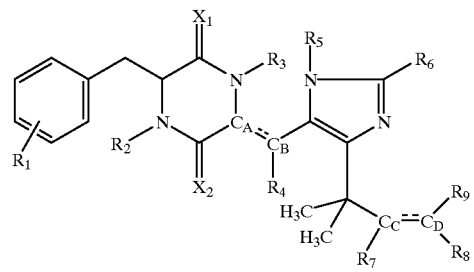

wherein $R_1$ to $R_9$ are defined; or a salt of the compound, and provides pharmaceutical compositions comprising a compound of the invention and a pharmaceutically acceptable carrier. The invention also provides methods of reducing or inhibiting mitosis of a cell by contacting the cell with a compound of the invention, which blocks the cell at the G2/M phase of the cell cycle. The invention also provides a method of reducing the severity of a pathology characterized, at least in part, by undesirable proliferation of a population of cells in a subject by administering to the subject a compound of the invention in an amount sufficient to reduce or inhibit proliferation of the population of cells.

4 Claims, No Drawings

HALIMIDE, A CYTOTOXIC MARINE NATURAL PRODUCT, AND DERIVATIVES THEREOF

This application is a continuation-in-part under CFR 1.53(b) (2) of prior application Ser. No. 09/047,781, filed Mar. 25, 1998 now abandoned, the entire contents of which are incorporated herein by reference.

This invention was made with government support under grants CA67775 awarded by the National Cancer Institute. The government has certain rights in the invention.

BACKGROUND OF THE INVENTION

1. Field of the Invention

This invention relates generally to the fields of biochemistry and medicine, and more specifically to a compounds useful as cancer chemotherapeutic agents.

2. Background Information

Cancer is a leading cause of death in the United States. Despite significant efforts to find new approaches for treating cancer, surgery, chemotherapy and radiation therapy, either alone or in combination, remain the methods of choice. Surgery and radiation therapy, however, generally are useful only for fairly defined cancers and are of limited use for treating patients with disseminated disease.

Chemotherapy is the method of choice for treating patients with metastatic cancer or patients with diffuse cancers such as leukemias. Although chemotherapy can provide a therapeutic benefit in many cancer patients, it often fails to result in cure of the disease due to the patient's cancer cells becoming resistant to the chemotherapeutic agent. Due, in part, to the likelihood of cancer cells becoming resistant to a chemotherapeutic agent, these drugs commonly are used in combination to treat patients.

A continuing effort is being made by individual investigators and by large pharmaceutical companies to identify new, potentially useful chemotherapeutic agents. In some cases, derivatives of known effective drugs are prepared and examined for improved or different, but useful characteristics. In addition, large libraries of randomly synthesized drugs have been prepared and the drugs then examined for potential efficacy as chemotherapeutic agents. Both of these methods have resulted in the identification of useful or potentially useful cancer chemotherapeutic agents.

Efforts also have been made to identify potentially useful drugs that are produced naturally by living organisms. For example, paclitaxel is a chemical that is produced by the yew tree and, when purified, is effective in treating cancers such as ovarian carcinoma. Despite the identification of such new chemotherapeutic agents, additional compounds that can be used to treat diseases such as cancer are needed. The present invention satisfies this need and provides additional advantages.

SUMMARY OF THE INVENTION

The present invention provides a substantially purified compound having the structure:

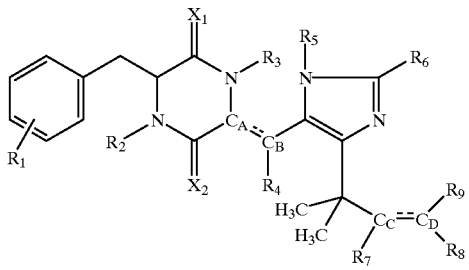

wherein $R_1$ is a hydrogen atom, hydroxyl, $C_1$ to $C_6$ alkyl, cycloalkyl, (cycloalkyl)alkyl, phenyl, phenylalkyl, (substituted)phenyl,(substituted) phenylalkyl), heteroaryl, (heteroaryl)alkyl, $C_1$ to $C_6$ alkoxy, halogen, amino, protected amino, an amino salt, mono-substituted amino, di-substituted amino, cyano or a nitro group;

$R_2$ and $R_3$ independently are a hydrogen atom, $C_1$ to $C_6$ alkyl, cycloalkyl, phenyl, (cycloalkyl)alkyl, (substituted) phenyl, phenylalkyl, (heteroaryl)alkyl, (substituted) phenylalkyl, heteroaryl or a $C_1$ to $C_6$ alkoxy group;

$R_4$ is a hydrogen atom, $C_1$ to $C_6$ alkyl, $C_1$ to $C_6$ alkoxy, $C_1$ to $C_6$ aryl, cycloalkyl, phenyl, phenylalkyl, (cycloalkyl) alkyl, (substituted)phenyl, heteroaryl, (substituted) phenylalkyl,(heteroaryl)alkyl, ketone, amino, protected amino, an amino salt, mono-substituted amino, di-substituted amino or a halogen group;

$R_5$ is a hydrogen atom, halogen, $C_1$ to $C_6$ alkyl, $C_1$ to $C_6$ alkoxy cycloalkyl, phenyl, (cycloalkyl)alkyl, (substituted) phenyl, phenylalkyl, heteroaryl, (substituted)phenylalkyl, (heteroaryl)alkyl, acetyl or a cyano group;

$R_6$ is a hydrogen atom, $C_1$ to $C_6$ alkyl or $C_1$ to $C_6$ alkoxy, cycloalkyl, phenyl, (cycloalkyl)alkyl, (substituted)phenyl, phenylalkyl, heteroaryl, (substituted)phenylalkyl, (heteroaryl)alkyl group or a bromine atom;

$R_7$ is a hydrogen atom, bromine, chlorine, fluorine, iodine, $C_1$ to $C_6$ alkyl, $C_1$ to $C_6$ alkoxy or $C_1$ to $C_6$ alkyne, $C_1$ to $C_6$ aryl, cycloalkyl, phenyl, (cycloalkyl)alkyl, (substituted)phenyl, phenylalkyl, heteroaryl, (substituted) phenylalkyl, (heteroaryl)alkyl halogen or amino, protected amino, an amino salt, mono-substituted amino or a di-substituted amino group;

$R_8$ is a hydrogen atom, bromine, chlorine, fluorine, iodine, $C_1$ to $C_6$ alkyl, $C_1$ to $C_6$ alkoxy, $C_1$ to $C_6$ alkyne, $C_1$ to $C_6$ aryl, cycloalkyl, phenyl, (cycloalkyl)alkyl, (substituted)phenyl, phenylalkyl, heteroaryl, (substituted) phenylalkyl, (heteroaryl)alkyl halogen or amino, protected amino, an amino salt, mono-substituted amino or a di-substituted amino;

$R_9$ is a hydrogen atom, bromine, chlorine, fluorine, iodine, $C_1$ to $C_6$ alkyl, $C_1$ to $C_6$ alkoxy or $C_1$ to $C_6$ alkyne, $C_1$ to $C_6$ aryl, cycloalkyl, phenyl, (cycloalkyl)alkyl, (substituted)phenyl, phenylalkyl, heteroaryl, (substituted) phenylalkyl, (heteroaryl)alkyl halogen, amino, protected amino, an amino salt, mono-substituted amino or a di-substituted amino;

wherein $X_1$ and $X_2$ independently represent a oxygen atom or a sulfur atom;

wherein the carbon atoms $C_A$ and $C_B$ can be linked by a double bond or a single bond with S or R configurations or any percentage mixture of the two confirmations as any of the chiral centers in the molecule;

wherein the carbon atoms $C_C$ and $C_D$ can be linked by a double bond or a single bond with S or R configurations or any percentage mixture of the two confirmations as any of the chiral centers in the molecule;

where $C_C$ and $C_D$ are linked by a single bond each maybe independently substituted with a bromine atom;

where $R_8$ is a phenyl moiety, it can have an S or R configuration relative to $C_D$;

or a salt of the compound. For example, the invention provides halimide having the chemical structure:

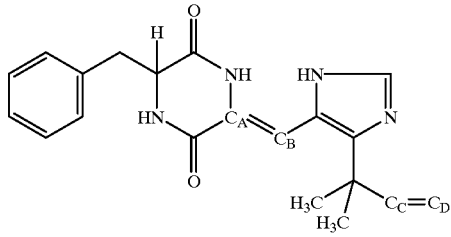

or a salt of halimide. The invention also provides pharmaceutical compositions comprising a compound of the invention, or a pharmaceutically acceptable salt thereof, and a pharmacologically acceptable carrier.

The invention also provides methods of reducing or inhibiting microtubule formation in a cell by contacting the cell with a compound of the invention. In addition, the invention provides methods of reducing or inhibiting mitosis of a cell by contacting the cell with a compound of the invention, which inhibits the cell in a premitotic stage of the cell cycle. As such, the invention provides a means for obtaining a population of cells containing a greater than normal percentage of cells in a premitotic stage.

The invention further provides a method of reducing or inhibiting the viability of a cell by contacting the cell with a compound of the invention. As such, the invention provides a method of reducing the severity of a pathology characterized, at least in part, by undesirable proliferation of a population of cells in a subject by administering to the subject a compound of the invention in an amount sufficient to reduce or inhibit proliferation of the population of cells. For example, the invention provides a method of treating a cancer patient by administering to the patient a compound of the invention in an amount sufficient to reduce or inhibit proliferation of cancer cells in the patient.

DETAILED DESCRIPTION OF THE INVENTION

The present invention provides a substantially purified compound having the general structure:

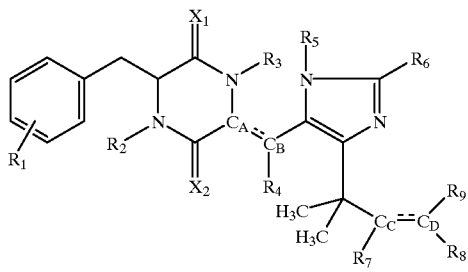

wherein $R_1$ is a hydrogen atom, hydroxyl, $C_1$ to $C_6$ alkyl, cycloalkyl, (cycloalkyl)alkyl, phenyl, (substituted)phenyl, phenylalkyl, (substituted) phenylalkyl), heteroaryl, (heteroaryl)alkyl, $C_1$ to $C_6$ alkoxy, halogen, amino, protected amino, an amino salt, mono-substituted amino, di-substituted amino, cyano or nitro group;

$R_2$ and $R_3$ independently are a hydrogen atom, $C_1$ to $C_6$ alkyl, cycloalkyl, phenyl, (cycloalkyl)alkyl, (substituted) phenyl, phenylalkyl, heteroaryl, (substituted)phenylalkyl, (heteroaryl)alkyl or a $C_1$ to $C_6$ alkoxy group;

$R_4$ is a hydrogen atom, $C_1$ to $C_6$ alkyl, $C_1$ to $C_6$ alkoxy, $C_1$ to $C_6$ aryl, cycloalkyl, phenyl, phenylalkyl, (cycloalkyl) alkyl, (substituted)phenyl, heteroaryl, (substituted) phenylalkyl, (heteroaryl)alkyl, ketone, amino, protected amino, an amino salt, mono-substituted amino, di-substituted amino or a halogen group;

$R_5$ is a hydrogen atom, halogen, $C_1$ to $C_6$ alkyl, $C_1$ to $C_6$ alkoxy cycloalkyl, phenyl, (cycloalkyl)alkyl, (substituted) phenyl, phenylalkyl, heteroaryl, (substituted)phenylalkyl, (heteroaryl)alkyl, acetyl or a cyano group;

$R_6$ is a hydrogen atom, $C_1$ to $C_6$ alkyl or $C_1$ to $C_6$ alkoxy, cycloalkyl, phenyl, (cycloalkyl)alkyl, (substituted)phenyl, phenylalkyl, heteroaryl, (substituted)phenylalkyl, (heteroaryl)alkyl or a bromine atom;

$R_7$ is a hydrogen atom, bromine, chlorine, fluorine, iodine, $C_1$ to $C_6$ alkyl, $C_1$ to $C_6$ alkoxy or $C_1$ to $C_6$ alkyne, $C_1$ to $C_6$ aryl, cycloalkyl, phenyl, (cycloalkyl)alkyl, (substituted)phenyl, phenylalkyl, heteroaryl, (substituted) phenylalkyl, (heteroaryl)alkyl halogen or amino, protected amino, an amino salt, mono-substituted amino or a di-substituted amino group;

$R_8$ is a hydrogen atom, bromine, chlorine, fluorine, iodine, $C_1$ to $C_6$ alkyl, $C_1$ to $C_6$ alkoxy, $C_1$ to $C_6$ alkyne, $C_1$ to $C_6$ aryl, cycloalkyl, phenyl, (cycloalkyl)alkyl, (substituted)phenyl, phenylalkyl, heteroaryl, (substituted) phenylalkyl, (heteroaryl)alkyl halogen or amino, protected amino, an amino salt, mono-substituted amino or a di-substituted amino;

$R_9$ is a hydrogen atom, bromine, chlorine, fluorine, iodine, $C_1$ to $C_6$ alkyl, $C_1$ to $C_6$ alkoxy or $C_1$ to $C_6$ alkyne, $C_1$ to $C_6$ aryl, cycloalkyl, phenyl, (cycloalkyl)alkyl, (substituted)phenyl, phenylalkyl, heteroaryl, (substituted) phenylalkyl, (heteroaryl)alkyl halogen, amino, protected amino, an amino salt, mono-substituted amino or a di-substituted amino;

wherein $X_1$ and $X_2$ independently represent a oxygen atom or a sulfur atom; and wherein the carbon atoms $C_A$ and $C_B$ can be linked by a double bond or a single bond with S or R configurations or any percentage mixture of the two confirmations as any of the chiral centers in the molecule;

wherein the carbon atoms $C_C$ and $C_D$ can be linked by a double bond or a single bond with S or R configurations or any percentage mixture of the two confirmations as any of the chiral centers in the molecule;

where $C_C$ and $C_D$ are linked by a single bond each maybe independently substituted with a bromine atom;

where $R_8$ is a phenyl moiety, it can have an S or R configuration relative to $C_D$;

or a salt of the compound. For example, the invention provides halimide having the chemical structure:

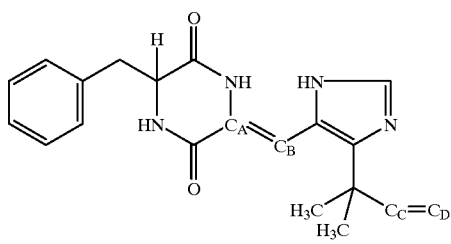

or a salt of halimide. The invention also provides various compounds having the above structure, except wherein $R_1$, $R_4$, $R_5$, $R_6$, $R_7$, $R_8$ and $R_9$ each is a hydrogen atom and $R_2$ and $R_3$ each is a methyl group ("compound A"); or wherein $R_1$, $R_2$, $R_3$, $R_4$, $R_5$, $R_7$, $R_8$ and $R_9$ each is a hydrogen atom and $R_6$ is a bromine atom ("compound B"); or wherein $R_1$, $R_2$, $R_3$, $R_4$, $R_6$, $R_7$, $R_8$ and $R_9$ each is a hydrogen atom and $R_5$ is an acetyl group ("compound C"); or wherein $R_1$, $R_2$, $R_3$, $R_4$, $R_5$, $R_6$, $R_7$, $R_8$ and $R_9$ each is a hydrogen atom, and $C_C$ and $C_D$ are linked by a single bond and $C_C$ and $C_D$ are each substituted with a bromine atom ("compound D"); or wherein $R_1$, $R_2$, $R_3$, $R_4$, $R_5$, $R_6$, $R_7$, $R_8$ and $R_9$ each is a hydrogen atom and $C_A$ and $C_B$ are linked by a single bond ("compound E").

Halimide is an aromatic alkaloid isolated from the fermentation of a marine fungus, Aspergillus sp. CNC139, which was collected in the waters off the Philippine Islands and has been deposited with the American Type Culture Collection as Accession No. 74434, date deposited Apr. 10, 1998 (Rockville Md.). Halimide is a diketopiperazine composed of two amino acid residues and represents the first cytotoxic molecule having anticancer activity discovered from this Aspergillus sp. As disclosed herein, the compounds of the invention, including halimide and derivatives thereof, can reduce or inhibit the progression of cells through mitosis of the cell cycle and, therefore, can reduce or inhibit cell proliferation and cell viability.

With respect to the general structure of a compound of the invention, the term "alkyl" means a straight or branched $C_1$ to $C_6$ carbon chain such as methyl, ethyl, tert-butyl, isopropyl, n-octyl, and the like. The terms "halo" and "halogen" refer to the fluoro, chloro, bromo or iodo groups. There can be one or more halogen, which are the same or different. Preferred halogens are bromo, chloro and fluoro. The term "aryl" refers to aromatic five and six membered carbocyclic rings such as heteroaryl. Six membered rings are preferred.

The term "heteroaryl" denotes optionally substituted five-membered or six-membered rings that have 1 to 4 heteroatoms, such as oxygen, sulfur or nitrogen atoms, in particular nitrogen, either alone or in conjunction with sulfur or oxygen ring atoms. These five-membered or six-membered rings are fully unsaturated. The following ring systems are provided as examples of a heterocyclic (whether substituted or unsubstituted) radical denoted, i.e., a heteroaryl: thienyl, furyl, pyrrolyl, pyrrolidinyl, imidazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, oxazinyl, triazinyl, thiadiazinyl tetrazolo, 1,5-(b)pyridazinyl and purinyl, as well as benzo-fused derivatives, for example, benzoxazolyl, benzothiazolyl, benzimidazolyl and indolyl.

Substituents for the above optionally substituted heteroaryl rings are from one to three halo, trihalomethyl, amino, protected amino, amino salts, mono-substituted amino, di-substituted amino, carboxy, protected carboxy, carboxylate salts, hydroxy, protected hydroxy, salts of a hydroxy group, lower alkoxy, lower alkylthio, alkyl, substituted alkyl, cycloalkyl, substituted cycloalkyl, (cycloalkyl) alkyl, substituted (cycloalkyl)alkyl, phenyl, substituted phenyl, phenylalkyl, and (substituted phenyl)alkyl groups. Substituents for the heteroaryl group are as heretofore defined, or as set forth below.

As used in conjunction with the above substituents for heteroaryl rings, "trihalomethyl" can be trifluoromethyl, trichloromethyl, tribromomethyl or triiodomethyl; "lower alkoxy" means a $C_1$ to $C_6$ alkoxy group; and "lower alkylthio" means a $C_1$ to $C_6$ alkylthio group. The term "substituted alkyl" means the above-defined alkyl group substituted from one to three times by a hydroxy, protected hydroxy, amino, protected amino, cyano, halo, trifluoromethyl, mono-substituted amino, di-substituted amino, lower alkoxy, lower alkylthio, carboxy, protected carboxy, or a carboxy, amino, and/or hydroxy salt.

As used in conjunction with the substituents for the heteroaryl rings, the terms "substituted (cycloalkyl)alkyl" and "substituted cycloalkyl" are as defined above substituted with the same groups as listed for a "substituted alkyl" group. The term "(monosubstituted)amino" refers to an amino group with one substituent chosen from the group consisting of phenyl, substituted phenyl, alkyl, substituted alkyl, $C_1$ to $C_6$ acyl, $C_1$ to $C_6$ alkenyl, $C_1$ to $C_6$ substituted alkenyl, $C_1$ to $C_6$ alkynyl, $C_1$ to $C_6$ alkylaryl, $C_1$ to $C_6$ substituted alkylaryl and heteroaryl group. The (monosubstituted)amino can additionally have an amino-protecting group as encompassed by the term "protected (monosubstituted)amino." The term "(disubstituted)amino" refers to amino groups with two substituents chosen from the group consisting of phenyl, substituted phenyl, alkyl, substituted alkyl, $C_1$ to $C_6$ acyl, $C_1$ to $C_6$ alkenyl, $C_1$ to $C_6$ alkynyl, $C_1$ to $C_6$ alkylaryl, $C_1$ to $C_6$ substituted alkylaryl and heteroaryl. The two substituents can be the same or different. The term "heteroaryl(alkyl)" denotes an alkyl group as defined above, substituted at any position by a heteroaryl group, as above defined.

Furthermore, the above optionally substituted five-membered or six-membered heterocyclic rings can optionally be fused to a aromatic 5-membered or 6-membered aryl or heteroaryl ring system. For example, the rings can be optionally fused to an aromatic 5-membered or 6-membered ring system such as a pyridine or a triazole system, and preferably to a benzene ring.

The term "salt" or "pharmaceutically-acceptable salt" encompasses those salts that form with the carboxylate anions and includes salts formed with the organic and inorganic cations such as those chosen from the alkali and alkaline earth metals, (for example, lithium, sodium, potassium, magnesium, barium and calcium); ammonium ion; and the organic cations (for example, dibenzylammonium, benzylammonium, 2-hydroxyethylammonium, bis(2-hydroxyethyl)ammonium, phenylethylbenzylammonium, dibenzylethylenediammonium, and like cations.) Other cations encompassed by the above term include the protonated form of procaine, quinine and N-methylglucosamine, the protonated forms of basic amino acids such as glycine, ornithine, histidine, phenylglycine, lysine, and arginine. Furthermore, any zwitterionic form of the instant compounds formed by a carboxylic acid and an amino group is referred to by this term. A preferred cation for the carboxylate anion is the sodium cation. Further included are salts that form by standard acid-base reactions with basic groups (such as amino groups), including organic or inorganic acids. Such acids include hydrochloric, sulfuric, phosphoric, acetic, succinic, citric, lactic, maleic, fumaric, palmitic, cholic, pamoic, mucic, D-glutamic, D-camphoric, glutaric, phthalic, tartaric, lauric, stearic, salicylic, methanesulfonic, benzenesulfonic, sorbic, picric, benzoic, cinnamic acids, and the like.

The compounds of the above structure may also exist as solvates and hydrates. Thus, these compounds may crystallize with, for example, waters of hydration, or one, a number of, or any fraction thereof of molecules of the mother liquor solvent. The solvates and hydrates of such compounds are included within the scope of this invention.

The term "hydroxy-protecting group" refers to readily cleavable groups bonded to hydroxyl groups, such as the tetrahydropyranyl, 2-methoxyprop-2-yl, 1-ethoxyeth-1-yl, methoxymethyl, β-methoxyethoxymethyl, methylthiomethyl, t-butyl, t-amyl, trityl, 4-methoxytrityl, 4,4'-dimethoxytrityl, benzyl, allyl, 4,4',4"-trimethoxytrityl, trimethylsilyl, (t-butyl)dimethylsilyl, 2,2,2-trichloroethoxycarbonyl, and the like. Further examples of hydroxy-protecting groups are described by Reese and Haslam, "Protective Groups in Organic Chemistry" (McOmie, Ed., Plenum Press, New York, N.Y., 1973), Chaps. 3 and 4; and Greene and Wuts, "Protective Groups in Organic Synthesis," Second Edition (John Wiley and Sons, New York, 1991), Chaps. 2 and 3; each of which is incorporated herein by reference. A preferred hydroxy-protecting group is the tert-butyl group. The related term "protected hydroxy" denotes a hydroxy group bonded to one of the above hydroxy-protecting groups.

The term "amino-protecting group" as used herein refers to substituents of the amino group commonly employed to block or protect the amino functionality while reacting other functional groups of the molecule. The term "protected (monosubstituted)amino" means there is an amino-protecting group on the monosubstituted amino nitrogen atom.

Examples of such amino-protecting groups include the formyl group, the trityl group, the phthalimido group, the trichloroacetyl group, the trifluoroacetyl group, the chloroacetyl, bromoacetyl, and iodoacetyl groups, urethane-type protecting groups, such
as t-butoxycarbonyl ("Boc"), 2-(4-biphenylyl) propyl-2-oxycarbonyl, 2-phenylpropyl-2-oxycarbonyl,
2-(4-xenyl)isopropoxycarbonyl, 1,1-diphenylethyl-1-oxycarbonyl, 1,1-diphenylpropyl-1-oxycarbonyl,
2-(3,5-dimethoxyphenyl)propyl-2-oxycarbonyl, 2-(p-toluyl) propyl-2-oxycarbonyl, cyclopentanyloxycarbonyl,
1-methylcyclopentanyl-oxycarbonyl, cyclohexanyloxycarbonyl, 1-methyl-cyclohexanyloxycarbonyl,
2-methylcyclohexanyl-oxycarbonyl, 2-(4-toluylsulfonyl) ethoxycarbonyl, 2-(methylsulfonyl)ethoxycarbonyl,
2-(triphenylphosphino)-ethoxycarbonyl,
9-fluorenylmethoxycarbonyl ("Fmoc"),
2-(trimethylsilyl)ethoxycarbonyl, allyloxycarbonyl,
1-(trimethylsilylmethyl)prop-1-enyloxycarbonyl,
5-benzisoxalylmethoxycarbonyl, 4-acetoxybenzyloxycarbonyl, 2,2,2-trichloroethoxycarbonyl,
2-ethynyl-2-propoxycarbonyl, cyclopropylmethoxycarbonyl,
isobornyloxycarbonyl, 1-piperidyloxycarbonyl,
benzyloxycarbonyl ("Cbz"), 4-phenylbenzyloxycarbonyl,
2-methylbenzyloxycarbonyl, 4-methoxybenzyloxycarbonyl,
α-2,4,5,-tetramethylbenzyl- oxycarbonyl,
4-fluorobenzyloxycarbonyl, 4-chlorobenzyloxycarbonyl,
3-chlorobenzyloxycarbonyl, 2-chlorobenzyloxycarbonyl,
2,4-dichlorobenzyloxycarbonyl, 4-bromobenzyloxycarbonyl,
3-bromobenzyloxycarbonyl, 4-nitrobenzyloxycarbonyl,
4-cyanobenzyloxycarbonyl, 4-(decyloxy) benzyloxycarbonyl and the like; the benzoylmethylsulfonyl group, the 2,2,5,7,8-pentamethylchroman-6-sulfonyl group, the dithiasuccinoyl group, the 2-(nitro)phenylsulfenyl group, the diphenylphosphine oxide group, and like amino-protecting groups.

The species of amino-protecting group employed is not critical so long as the derivatized amino group is stable to the conditions of the subsequent reaction(s) and can be removed at the appropriate point without disrupting the remainder of the molecule. Preferred amino-protecting groups are Boc, Cbz and Fmoc. Further examples of amino-protecting groups embraced by the above term are well known in organic synthesis and the peptide art and are described, for example, by Greene and Wuts, supra, 1991, Chap. 7; Bodanzsky, "Principles of Peptide Synthesis," 1st and 2nd revised Ed. (Springer-Verlag, N.Y., 1984 and 1993); Stewart and Young, "Solid Phase Peptide Synthesis," 2nd Ed. (Pierce Chemical Co., Rockford Ill., 1984); Atherton and Shephard, "Solid Phase Peptide Synthesis—A Practical Approach" (IRL Press, Oxford England, 1989), each of which is incorporated herein by reference. The related term "protected amino" defines an amino group substituted with an amino-protecting group discussed above.

Depending on the choice of solvent and other conditions known to the practitioner skilled in the art, compounds of this invention may also take the ketal or acetal form, which forms are included in the instant invention. In addition, it should be understood that the equilibrium forms of the compounds of this invention may include tautomeric forms. All such forms of these compounds are expressly included in the present invention.

The compounds of the invention can be modified by appropriate functionalities to enhance selective biological properties. Such modifications are known in the art and include those which increase biological penetration into a given biological system, for example, blood, the lymphatic system, or the central nervous system, increase oral availability, increase solubility to allow administration by injection, alter metabolism and alter rate of exertion. In addition, the compounds can be altered to a pro-drug form such that the desired compound is created in the body of the patient as the result of the action of metabolic or other biochemical processes on the pro-drug. Some examples of pro-drug forms include ketal, acetal, oxime, and hydrazone forms of compounds which contain ketone or aldehyde groups.

The compounds of the invention, including derivatives of halimide, can be synthesized using conventional techniques as disclosed herein (see Example II). Advantageously, these compounds are conveniently synthesized from readily available starting materials. As disclosed herein, a compound of the invention, halimide, can be isolated in substantially purified form from Aspergillus sp. CNC139, then can be chemically modified as desired to contain one or more of the substituents discussed above. As used herein, the term "isolated" or "substantially purified" means that the compound of the invention is at least about 50% free of materials with which it normally is associated in a cell, particularly CNC139, and generally is about 90% or 95% free of such materials, particularly at least 99% free of such material.

If desired, a compound of the invention can be in the form of a pharmaceutical composition, comprising the compound or a salt thereof, and a pharmaceutically acceptable carrier. Pharmaceutically acceptable carriers, which can be an adjuvant or other vehicle, include, but are not limited to, ion exchange resins, alumina, aluminum stearate, lecithin, serum proteins, such as human serum albumin; buffer substances such as the various phosphates, glycine, sorbic acid, potassium sorbate, partial glyceride mixtures of saturated vegetable fatty acids; water, salts or electrolytes, such as protamine sulfate, disodium hydrogen phosphate, potassium hydrogen phosphate, sodium chloride, and zinc salts; colloidal silica, magnesium trisilicate, polyvinyl pyrrolidone, cellulose-based substances, polyethylene glycol, sodium carboxymethylcellulose, polyarylates, waxes, polyethylene-polyoxypropylene-block polymers, polyethylene glycol and wool fat, and the like.

A compound of the invention, when administered to a subject such as a mammalian subject, for example, a human, can be administered orally, parenterally, by inhalation, topically, rectally, nasally, buccally or vaginally, and can be contained in an implanted reservoir. Parenteral administration can be by subcutaneous, intracutaneous, intravenous, intramuscular, intra-articular, intrasynovial, intrasternal, intrathecal, intralesional or intracranial injection or by an infusion method.

A compound of the invention, which can comprise a pharmaceutical composition, can be in the form of a sterile injectable preparation, for example, a sterile injectable aqueous or oleaginous suspension. Such a suspension can be formulated by methods known in the art using, for example, suitable dispersing or wetting agents such as Tween 80, or suspending agents. The sterile injectable preparation also can be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic saline solution. In addition, sterile, fixed oils are conventionally employed as a solvent or suspending medium. For this purpose, any bland fixed oil can be employed, including synthetic monoglycerides or diglycerides. Fatty acids such as oleic acid and its glyceride derivatives also are useful in the preparation of injectables, as are natural pharmaceutically acceptable oils such as olive oil or castor oil, especially in their polyoxyethylated versions. These oil solutions or suspensions also can contain a long chain alcohol diluent or dispersant.

A compound of the invention can be orally administered in any orally acceptable dosage form including, but not limited to, capsules, tablets and aqueous suspensions and solutions. In the case of tablets for oral use, carriers that commonly are used include lactose and corn starch. Lubricating agents such as magnesium stearate also can be added. For oral administration in capsule form, useful diluents include lactose and dried corn starch. When aqueous suspensions are administered orally, the active ingredient can be combined with emulsifying and suspending agents. If desired, certain sweetening, flavoring or coloring agents can be added.

A compound of the invention also can be formulated in a pharmaceutical composition for administration in the form of suppositories for rectal administration. Such a composition can be prepared by mixing a compound of the invention, for example, halimide, with a suitable non-irritating excipient that is solid at room temperature, but liquid at the rectal temperature. Such materials include, but are not limited to, cocoa butter, beeswax and polyethylene glycols.

Topical administration of a compound of the invention can be particularly useful when the desired treatment involves areas or organs readily accessible to topical application. For application topically to the skin, for example, the compound should be formulated with a suitable ointment containing the active compound suspended or dissolved in a carrier, or can be in the form of a spray. Carriers for topical administration of the compounds of the invention include, but are not limited to, mineral oil, liquid petroleum, white petroleum, propylene glycol, polyoxyethylene, polyoxypropylene compound, emulsifying wax and water. A compound of the invention also can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. A compound also can be formulated to allow topically application to the lower intestinal tract by rectal suppository formulation or in a suitable enema formulation. Topically applied transdermal patches containing a compound of the invention are also included in this invention.

A compound of the invention also can be administered by nasal aerosol or inhalation. Such compositions are prepared according to techniques well known in the art of pharmaceutical formulation and can be prepared as solutions in saline, employing benzyl alcohol or other suitable preservatives, absorption promoters to enhance bioavailability, fluorocarbons, or other solubilizing or dispersing agents.

The compounds of the invention also are provided as commercial reagents, which are useful, for example, for reducing or inhibiting polymerization of tubulin, either in vitro or in cells in culture or in situ, or for blocking progression of cells through the cell cycle, or reducing or inhibiting cell proliferation or cell viability (see Examples III and IV). Thus, the invention provides methods of reducing or inhibiting cell proliferation or cell viability by contacting the cell with a compound of the invention, which blocks the cell in a premitotic stage of the cell cycle.

As disclosed herein, a compound of the invention reduces or inhibits tubulin polymerization and, therefore, microtubule formation is reduced or inhibited in a cell that is contacted with a compound of the invention. As a result, spindle fiber formation is reduced or inhibited and the cells are blocked in a premitotic stage. The cell cycle, which is the time between mitosis of a parent cell and mitosis of its progeny daughter cells, is defined by a series of stages, designated, G1, S, G2 and M, that the cell passes through. In general, in the G1 phase of the cell cycle, cells perform the specific functions normally associated with the particular cell type and prepare for the subsequent stage, in which DNA synthesis occurs. In the S phase, DNA synthesis occurs, such that the genomic complement is duplicated as the cell prepares to divide into two daughter cells. In the G2 phase, the cells further prepare for cell division, and in the M phase, the cells undergo mitosis, resulting in the production of two daughter cells.

The M phase of the cell cycle is further divided into prophase, during which the duplicated chromosomes condense; metaphase, during which the condensed chromosomes line up at an equatorial position in the cell; anaphase, during which a single complement of chromosomes is drawn to each of poles of the cell, due to the action of the spindle apparatus, and the cell begins to divide along the equatorial plane; and telophase, during which cell division is completed, to produce two daughter cells, and the chromosomes decondense.

Cell division is dependent, in part, on the formation of a spindle apparatus, which is formed by the polymerization of tubulin. Elements of the spindle apparatus attach to each chromosome and are involved in segregation of a single complement of chromosomes to each of the two daughter cells. When spindle formation is inhibited, the chromosomes do not segregate to the poles of the cell and the cells do not divide. Instead, the cells are blocked at the G2/M boundary and are maintained in this premitotic stage. If cells are maintained in this premitotic stage for a prolonged period of time, they will die due to a lack of the normal metabolic activity required to maintain the cells.

A class of compounds, the vinca alkaloids, which include colchicine, vinblastine and vincristine, bind to tubulin and inhibit its polymerization. As such, cells contacted with a vinca alkaloid cannot form spindle fibers during mitosis and, therefore, are blocked in a premitotic state. Because of their activity, vinca alkaloids have numerous uses. For example, the mitotic stage of the cell cycle normally constitutes only a small percentage of the total cell cycle time and, therefore, in a given population of cells, only a small percentage of the cells, about 0.5 to 2%, will be in M phase at any given time. Vinca alkaloids such as colchicine commonly are used to treat cells in culture in order to increase the percentage of cells in M phase in the population of cells. For example, colchicine treatment is used to prepare cells for chromosome staining, which requires a relatively large number of cells having condensed chromosomes, as occurs during M phase.

Vinca alkaloids also are used to reduce or inhibit the survival of cells because, as discussed above, cells that are blocked in a premitotic stage die if the block is maintained. In particular, vinca alkaloids are useful for killing rapidly dividing cells such as cancer cells and, therefore, often are used for treating cancer patients.

As disclosed herein, halimide inhibits tubulin polymerization. For example, incubation of 2X cycled bovine brain tubulin, in the presence of GTP, with 20 $\mu$M halimide, inhibited tubulin polymerization by 55%. Thus, the compounds of the invention have an activity similar to vinca alkaloids, but are chemically distinct from the vinca alkaloids. These results indicate that a compound of the invention such as halimide can inhibit spindle formation in cells, thus reducing or inhibiting the ability of the cells to proceed through mitosis and arresting the cells in a premitotic stage.

As used herein, the term "premitotic stage," when used in reference to cells, means that the cells have not attained the anaphase stage of mitosis and, therefore, have not yet begun to divide. As disclosed herein, incubation of carcinoma cells in the presence of 5 $\mu$M halimide arrested the cells at or near the G2/M boundary of the cell cycle and, therefore, results in an accumulation of the cells in a premitotic stage. Thus, the invention provides a method of reducing or inhibiting the ability of the cells to proceed through mitosis and, therefore, proliferate, by contacting the cells with a compound of the invention.

The term "reducing or inhibiting" is used variously herein to mean that a parameter is decreased due to an action of a compound of the invention as compared to the parameter in the absence of any action by a compound of the invention. For example, the term "reducing or inhibiting," when used in reference to spindle fiber formation, means that the amount of spindle formation is decreased in cells treated with a compound of the invention as compared to untreated cells. Similarly, the term "reducing or inhibiting," when used in reference to cell viability or to cell proliferation, means that survival or proliferative activity of cells contacted with a compound of the invention is less than the survival or proliferation in the absence of the compound. The terms "reduce" and "inhibit" are used together herein because it is recognized that, depending on the particular assay used to examine a parameter, the limit of detection of the assay may be such that it will not be able to be determined whether the parameter is inhibited or is reduced below the level of detection of the assay. For example, the ability of the cells to proceed through mitosis in the presence of a compound of the invention may be completely inhibited, i.e., 100% of the cells are blocked in a premitotic stage, or may be reduced such that 90% or 99% of the cells are blocked in a premitotic stage. It should be recognized, however, that regardless of whether the recited parameter is "reduced" or is "inhibited," the level of the parameter as determined in the presence of a compound of the invention will be measurably decreased as compared to the level the parameter would be in the absence of the compound.

Upon contacting a population of cells with a compound of the invention, the cells accumulate in a premitotic stage, resulting in a population of cells containing a greater than normal percentage of cells in a premitotic stage. Such a population of cells is useful, for example, for examining chromosome structure in the cells, since the chromosomes in such blocked premitotic cells are present in a condensed state. Such cells are suitable, for example, for chromosome staining using well known methods such as Giemsa staining or quinacrine staining to perform G band or C band analysis or the like. In addition, the ability to increase the percentage of cells in a premitotic stage allows for the isolation of a synchronized population of cells, for example, by fluorescence activated cell sorting or, where the cells normally attach to a tissue culture plate, by shaking rounded, detached premitotic cells from the plate, as is known in the art.

The invention further provides a method of reducing or inhibiting the proliferative ability or the viability of a cell by contacting the cell with a compound of the invention. As such, the invention provides a method of reducing the severity of a pathology characterized, at least in part, by undesirable proliferation of a population of cells in a subject by administering to the subject a compound of the invention in an amount sufficient to reduce or inhibit the amount of proliferation of the population of cells. Such an amount of a compound of the invention is an amount that reduces or inhibits tubulin polymerization in the cells and, therefore, blocks the cells in a premitotic stage. For example, the invention provides a method of treating a cancer patient by administering to the patient a compound of the invention in an amount sufficient to reduce or inhibit proliferation of cancer cells in the patient.

As disclosed herein, halimide produced a dose dependent cytotoxic effect against a variety of tumor cell lines, including human colon HCT116 cells ($IC_{50}$=1 $\mu$M) and human ovarian A2780 cells ($IC_{50}$=0.82 $\mu$M), where "$IC_{50}$" indicates the drug concentration required to inhibit cell proliferation by 50% as compared to untreated cells (Example III). In addition, halimide treatment produced a 53% increase in life span in an intraperitoneal injected P388 in vivo murine leukemia model (Example IV). Thus, the invention provides a method of treating a cancer patient by administering to the patient a compound of the invention in an amount sufficient to reduce or inhibit proliferation of cancer cells in the patient.

A compound of the invention such as halimide provides advantages over the use of vinca alkaloids clinically because the compounds of the invention are chemically distinct from vinca alkaloids and, therefore, cells that have become resistant to vinca alkaloids are not cross-resistant to the compounds of the invention. For example, multi-drug resistant human colon carcinoma cells were not resistant to halimide.

In addition, halimide was collaterally sensitive in a paclitaxel-resistant A2780 cell line with altered tubulin. Halimide also can hyperphosphorylate Bcl-2 and, therefore, can be useful for altering the likelihood that a cell will undergo apoptosis.

In the studies disclosed herein, halimide inhibited tubulin polymerization. Each molecule of halimide bound tightly to one tubulin molecule and inhibited its polymerization. Exposure of dividing cells to halimide caused disappearance of the mitotic spindle and blocked the cell in a premitotic stage within a few minutes; the cells did not divide. Since cancer cells generally divide more rapidly than their normal cell counterpart, cancer cells generally are more susceptible than the normal cells to mitotic inhibitors such as halimide.

The following examples are intended to illustrate but not limit the invention.

EXAMPLE I

PRODUCTION AND PURIFICATION OF HALIMIDE

The halimide producing strain, tentatively identified as an Aspergillus sp., designated CNC139, was isolated from a sample of the green alga *Halimeda copiosa*. Aspergillus sp. CNC139 has been deposited with the American Type Culture Collection as Accession No. 74434, date deposited Apr. 10, 1998. Halimide was purified from the CNC139 cells.

CNC139 was inoculated into 10 ml of the marine based medium YPG, consisting of 0.5% yeast extract, 0.5% peptone, 1% glucose in 100% seawater (United States Biochemical Corp.; Cleveland Ohio). After 5 days of static culture, the culture was transferred to 1 liter of the same medium and allowed to incubate for 21 days without shaking at 27° C.

Following fermentation, the mycelium was separated from the broth by filtration and the broth extracted twice with 1 liter volumes of ethyl acetate. The combined ethyl acetate extracts were dried over anhydrous sodium sulfate, filtered and concentrated by rotary evaporation. The crude extract was subjected to silica chromatography using a solvent gradient from 100% hexane to 100% ethyl acetate. The fractions were analyzed using NMR spectroscopy and those rich in halimide were combined and subjected to normal phase silica (5 $\mu$m) HPLC using a differential refractometer and 100% ethyl acetate. Peaks representing halimide were collected and final purification was achieved by crystallization in ethyl acetate. The structure of this compound was elucidated by combined mass spectrometry, proton and carbon NMR analyses (see Tables 1 and 2).

EXAMPLE II

SYNTHESIS OF A HALIMIDE DERIVATIVES

This example provides methods for synthesizing five different compounds of the invention using halimide as a starting material.

A compound of the invention, "compound E," having the general structure disclosed herein, but wherein $R_1$, $R_2$, $R_3$, $R_4$, $R_5$, $R_6$, $R_7$, $R_8$ and $R_9$ each is a hydrogen atom and $C_A$ and $C_B$ are linked by a single bond, is synthesized as follows. A solution containing 3 mg of halimide and 0.5 ml of methanol is combined with 1 mg of palladium on activated carbon (10%). The reaction mixture is stirred at room temperature under a hydrogen atmosphere for 12 hours and then poured onto water and extracted with ethyl acetate. The organic solution is dried over sodium sulfate and evaporated in a vacuum. The crude product is purified by silica HPLC (100% ethyl acetate) to yield the title substance.

A compound of the invention, "compound A," having the general structure disclosed herein, but wherein $R_1$, $R_4$, $R_5$, $R_6$, $R_7$, $R_8$ and $R_9$ each is a hydrogen atom and $R_2$ and $R_3$ each is a methyl group, is synthesized as follows. A solution of 5 mg of halimide in 1 ml of tetrahydrofuran is mixed with 0.2 ml of iodomethane and a solution of sodium hydride in dimethylformamide is added. After stirring of the reaction mixture for 1.5 hours at room temperature, the mixture is poured onto 0.1 M aqueous HCl, extracted with ethyl acetate and partitioned between ethyl acetate and saturated aqueous bicarbonate solution. The organic phase is washed with brine, dried over sodium sulfate and evaporated in vacuo. The crude product is purified by silica HPLC (100% ethyl acetate) to yield compound A.

A compound of the invention, "compound B," having the general structure disclosed herein, but wherein $R_1$, $R_2$, $R_3$, $R_4$, $R_5$, $R_7$, $R_8$ and $R_9$ each is a hydrogen atom and $R_6$ is a bromine atom, is synthesized as follows. A solution of 5 mg of halimide in 1 ml of tetrahydrofuran is mixed with pyridium tribromide in 0.5 ml of tetrahydrofuran at room temperature for 2 hours and 5 ml of 5% aqueous sodium bicarbonate is added. The reaction mixture is extracted with ethyl acetate. The organic phase is dried over sodium sulfate and evaporated in vacuo. The crude product is purified by silica HPLC (100% ethyl acetate) to yield compound B.

A compound of the invention, "compound C," having the general structure disclosed herein, but wherein $R_1$, $R_2$, $R_3$, $R_4$, $R_6$, $R_7$, $R_8$ and $R_9$ each is a hydrogen atom and $R_5$ is an acetyl group, is synthesized as follows. A solution of 5 mg halimide in 1 ml of acetic anhydride is mixed with potassium hydride at 0° C. under nitrogen atmosphere. The resulting solution is stirred at room temperature for 8 hours and then cooled in a bath as 5% aqueous sodium bicarbonate is added. The aqueous layer is extracted with ethyl acetate. The organic phase is dried over sodium sulfate and evaporated in vacuo. The crude product is purified by silica HPLC (100% ethyl acetate) to yield compound C.

A compound of the invention, "compound D," having the general structure disclosed herein, but wherein $R_1$, $R_2$, $R_3$, $R_4$, $R_5$, $R_6$, $R_7$, $R_8$ and $R_9$ each is a hydrogen atom and $C_C$ and $C_D$ are linked by a single bond and each substituted with a bromine atom, is synthesized as follows. A solution of 5 mg of halimide in 1 ml of chloroform is mixed with a solution of bromine in carbon tetrachloride. The solution is stirred at room temperature for 2 hours and 5 ml of 5% aqueous sodium bicarbonate is added. The resulting mixture is extracted with ethyl acetate. The organic solution is dried over sodium sulfate and evaporated in vacuo. The crude product is purified by silica HPLC (100% ethyl acetate) to yield compound D.

EXAMPLE III

HALIMIDE INHIBITS GROWTH OF COLON CARCINOMA CELLS AND OF OVARIAN CANCER CELLS IN VITRO

The cytotoxicity of halimide was assessed in vitro against the human colon carcinoma cell line HCT116 and the human ovarian carcinoma cell line A2780 by MTS assay (Ribs et al., *Mol. Biol. Cell* 3:184a (1992), which is incorporated herein by reference). Cells were plated at 4,000 cells/well in 96 well microliter plates and, after 24 hours, halimide (dissolved in DMSO) was added and serially diluted. The cells were incubated with the compound at 37° C. for 72 hours, then the tetrazolium dye MTS was added to a final concentration of 333 µg/ml and the electron coupling agent phenazine methosulfate was added to a final concentration of 25 µM. A dehydrogenase enzyme in live cells reduces the MTS to a form that absorbs light at 492 nM, which can be quantitated spectrophotometrically.

Assay results are expressed as an $IC_{50}$, which is the drug concentration required to inhibit cell proliferation by 50% compared to growth of untreated control cells. Halimide demonstrated potent cytotoxic activity against HCT116 human colon carcinoma cells ($IC_{50}$=1 µM) and A2780 human ovarian carcinoma cells ($IC_{50}$=0.8 µM). These results demonstrate that halimide is cytotoxic against various cancer cells in vitro.

EXAMPLE IV

HALIMIDE TREATMENT PROLONGS SURVIVAL OF MICE IN A LEUKEMIA MODEL

This example demonstrates that halimide treatment prolongs the survival of leukemic mice.

The efficacy of halimide was determined in vivo in a mouse P388 model. $1 \times 10^6$ P388 mouse leukemia cells were implanted in the intraperitoneal cavity of BALB/cX DBA/2 F1 (CDF1) or C57/BL6XDBA/2 F1 (BDF1) mice (Rose et al., Cancer Res. 43:1504–1510 (1983), which is incorporated herein by reference). Halimide was dissolved in ethanol and diluted with water to a concentration of 2.7 mg/ml. Halimide was injected intraperitoneally or intravenously beginning on the first day after tumor implantation and every day thereafter for five treatments. Increases in life span were reflected by the median survival time of treated (T) versus control (C) groups; T/C was calculated. For the P388 tumor model, a T/C less than or equal to 125% is considered to be a significant increase in survival. An optimal dose of 27 mg/kg/injection, ip, produced a T/C of 153%.

These results demonstrate that halimide significantly prolongs the survival of leukemia bearing mice.

Although the invention has been described with reference to the examples provided above, it should be understood that various modifications can be made without departing from the spirit of the invention. Accordingly, the invention is limited only by the claims.

We claim:

1. A substantially purified compound having the structure:

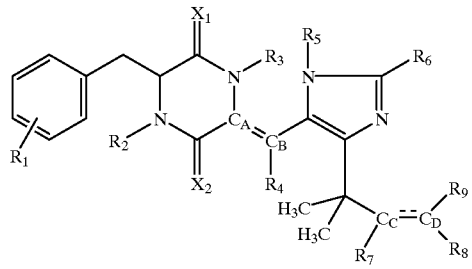

wherein, $R_1$, $R_2$, $R_3$, $R_4$, $R_5$, $R_6$, $R_7$, $R_8$ and $R_9$ each is a hydrogen atom, and $X_1$ and $X_2$ each is an oxygen atom, said compound which is halimide.

2. A substantially purified compound having the structure:

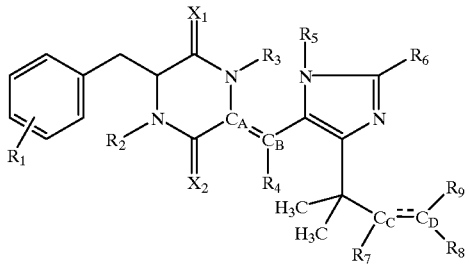

wherein, $R_1$, $R_4$, $R_5$, $R_6$, $R_7$, $R_8$ and $R_9$ each is a hydrogen atom, $X_1$ and $X_2$ each is an oxygen atom, and $R_2$ and $R_3$ each is a methyl group.

3. A substantially purified compound having the structure:

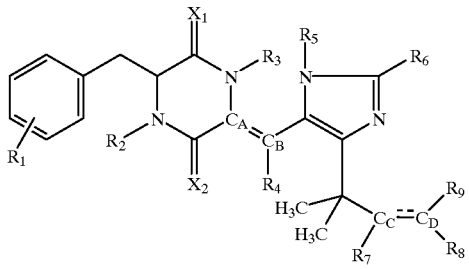

wherein, $R_1$, $R_2$, $R_3$, $R_4$, $R_6$, $R_7$, $R_8$ and $R_9$ each is a hydrogen atom, $X_1$ and $X_2$ each is an oxygen atom, and $R_5$ is an acetyl group.

4. A substantially purified compound having the structure:

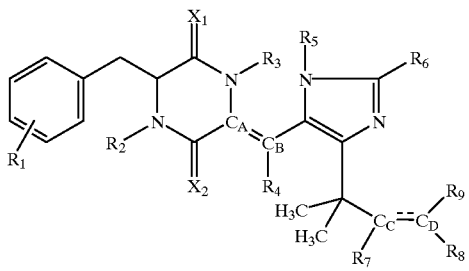

wherein, $R_1$, $R_2$, $R_3$, $R_4$, $R_5$, $R_7$, $R_8$ and $R_9$ each is a hydrogen atom, $X_1$ and $X_2$ is each an oxygen atom, and $R_6$ is a bromine atom.

* * * * *